United States Patent
Jung et al.

(10) Patent No.: US 7,994,097 B2
(45) Date of Patent: Aug. 9, 2011

(54) MICROARRAY, SUBSTRATE FOR MICROARRAY AND METHODS OF FABRICATING THE SAME

(75) Inventors: Sun-Ok Jung, Suwon-si (KR); Song-Jun Choi, Seoul (KR); Man-Hyoung Ryoo, Hwaseong-si (KR); Sung-Min Chi, Hwaseong-si (KR); Jung-Hwan Hah, Hwaseong-si (KR); Kyoung-Seon Kim, Suwon-si (KR); Won-Sun Kim, Suwon-si (KR)

(73) Assignee: SAMSUNG Electronics Co., Ltd., Suwon-si (KR)

( * ) Notice: Subject to any disclaimer, the term of this patent is extended or adjusted under 35 U.S.C. 154(b) by 345 days.

(21) Appl. No.: 12/137,608

(22) Filed: Jun. 12, 2008

(65) Prior Publication Data

US 2009/0137426 A1  May 28, 2009

(30) Foreign Application Priority Data

Jun. 12, 2007  (KR) .................. 10-2007-0057459

(51) Int. Cl.
  C40B 40/00  (2006.01)
  C40B 40/06  (2006.01)
  G01N 33/543  (2006.01)
  C12Q 1/68  (2006.01)

(52) U.S. Cl. .................. 506/13; 506/16; 506/23; 435/6; 436/518; 422/50

(58) Field of Classification Search ...... 435/6; 436/518; 422/50; 506/13, 16, 23
See application file for complete search history.

(56) References Cited

U.S. PATENT DOCUMENTS

| | | | | |
|---|---|---|---|---|
| 6,020,215 A | * | 2/2000 | Yagi et al. ................ | 438/52 |
| 6,506,558 B1 | * | 1/2003 | Fodor et al. .............. | 506/16 |
| 2003/0186228 A1 | * | 10/2003 | McDevitt et al. ........ | 435/6 |
| 2006/0134656 A1 | | 6/2006 | Hamers et al. | |

FOREIGN PATENT DOCUMENTS

JP  2003-121442  4/2003
KR  2003-54809  7/2003

* cited by examiner

*Primary Examiner* — Jezia Riley
(74) *Attorney, Agent, or Firm* — Stanzione & Kim, LLP

(57) ABSTRACT

A microarray, a substrate for a microarray and more productive methods of fabricating the microarray and the substrate are provided. The microarray includes a substrate divided into a first region and a second region; a plurality of linkers represented by formula 1 or 2:

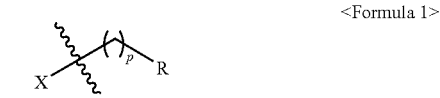

<Formula 1>

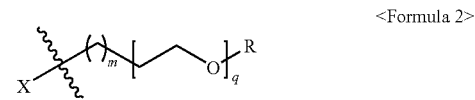

<Formula 2> wherein X is a site coupled to the substrate, R is a hydroxyl, aldehyde, carboxyl, amino, amide, thiol, halo, epoxy, or sulfonate group, m is an integer in the range of 3 to 16, p is an integer in the range of 1 to 30, and q is an integer in the range of 1 to 15,
directly coupled to the substrate in the first region but not coupled to the substrate in the second region; and
a plurality of probes coupled to the respective linkers.

23 Claims, 9 Drawing Sheets

102

201

MICROARRAY, SUBSTRATE FOR MICROARRAY AND METHODS OF FABRICATING THE SAME

CROSS-REFERENCE TO RELATED APPLICATIONS

This application claims priority from Korean Patent Application No. 10-2007-0057459 filed on Jun. 12, 2007 in the Korean Intellectual Property Office, the disclosure of which is incorporated herein by reference in its entirety.

BACKGROUND OF THE INVENTION

1. Field of the Invention

The present general inventive concept relates to a microarray, a substrate for a microarray and methods of fabricating the microarray and the substrate, and, more particularly, to a microarray having improved productivity, a substrate for a microarray and methods of fabricating the microarray and the substrate.

2. Description of the Related Art

In recent years, with the advance of genome projects, the genomic nucleotide sequences of various organisms have been identified. Thus, there has been an increasing interest in biopolymer microchips, in particular oligomer probe arrays. Microarrays are tools that have been widely used in gene expression profiling, genotyping, detection of mutation or polymorphism such as Single-Nucleotide Polymorphism (SNP), assaying of proteins or peptides, potential drug screening, and development and preparation of novel drugs.

To enable such assay or detection, a microarray includes a plurality of oligomer probes provided on a substrate. The plurality of oligomer probes have different sequences on different regions and are immobilized on the substrate. In order to immobilize the oligomer probes in a more secure, integrated manner, an active layer serving to mediate coupling of the oligomer probes may be formed on the substrate. Then, the active layer is patterned using the microarray, and a functional group is affixed on the patterned active layer, thereby completing fabrication of the microarray. As such, the conventional microarray fabricating process involves a number of complex processing steps.

SUMMARY OF THE INVENTION

The present general inventive concept provides a microarray that can be fabricated more easily.

The present general inventive concept also provides a substrate for the microarray.

The present general inventive concept also provides a method of fabricating a microarray having improved productivity.

Additional aspects and utilities of the present general inventive concept will be set forth in part in the description which follows and, in part, will be obvious from the description, or may be learned by practice of the general inventive concept.

The foregoing and/or other aspects and utilities of the present general inventive concept may be achieved by providing a microarray including a substrate divided into a first region and a second region, a plurality of linkers represented by formula 1 or 2, directly coupled to the substrate in the first region, but not coupled to the substrate in the second region, and a plurality of probes coupled to the respective linkers:

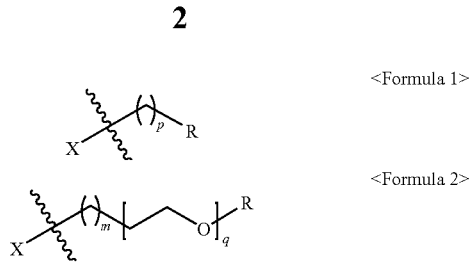

wherein X is a site coupled to the substrate, R is a hydroxyl, aldehyde, carboxyl, amino, amide, thiol, halo, epoxy, or sulfonate group, m is an integer in the range of 3 to 16, p is an integer in the range of 1 to 30, and q is an integer in the range of 1 to 15.

The foregoing and/or other aspects and utilities of the present general inventive concept may also be achieved by providing a microarray including a substrate divided into a first region and a second region, and a plurality of linkers represented by formula 1 or 2, directly coupled to the substrate in the first region, but not coupled to the substrate in the second region:

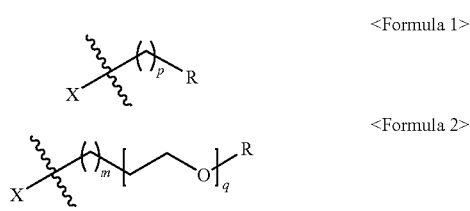

wherein X is a site coupled to the substrate, R is a hydroxyl, aldehyde, carboxyl, amino, amide, thiol, halo, epoxy, or sulfonate group, m is an integer in the range of 3 to 16, p is an integer in the range of 1 to 30, and q is an integer in the range of 1 to 15.

The foregoing and/or other aspects and utilities of the present general inventive concept may also be achieved by providing a method of fabricating a microarray including providing a substrate divided into a first region and a second region, directly coupling a plurality of linkers represented by formula 1 or 2 to the substrate in the first region, and coupling a plurality of probes to the respective linkers:

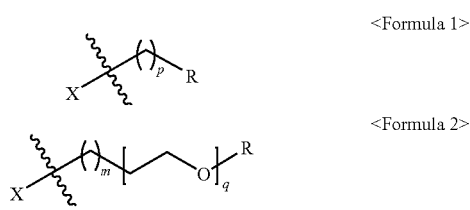

wherein X is a site coupled to the substrate, R is a hydroxyl, aldehyde, carboxyl, amino, amide, thiol, halo, epoxy, or sulfonate group, m is an integer in the range of 3 to 16, p is an integer in the range of 1 to 30, and q is an integer in the range of 1 to 15.

The foregoing and/or other aspects and utilities of the present general inventive concept may also be achieved by providing a method of fabricating a microarray including providing a substrate divided into a first region and a second region, laminating a linker compound represented by the compound 3 or 4, forming a plurality of linkers directly coupled to the substrate by selectively radiating UV light into the linker compound, and coupling probes to the plurality of linkers, respectively:

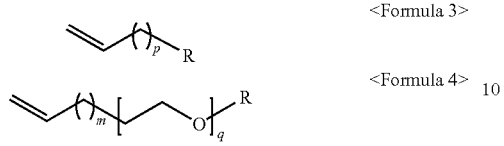

<Formula 3>

<Formula 4> wherein R is a hydroxyl, aldehyde, carboxyl, amino, amide, thiol, halo, epoxy, or sulfonate group, m is an integer in the range of 3 to 16, p is an integer in the range of 1 to 30, and q is an integer in the range of 1 to 15.

The foregoing and/or other aspects and utilities of the present general inventive concept may also be achieved by providing a method of fabricating a microarray, including: directly coupling a plurality of linkers represented by formula 1 or 2 to a first region of a substrate; and coupling a plurality of probes to the respective linkers:

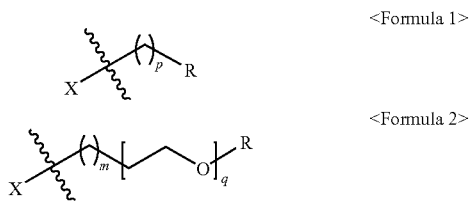

<Formula 1>

<Formula 2> wherein X is a site coupled to the substrate, R is a hydroxyl, aldehyde, carboxyl, amino, amide, thiol, halo, epoxy, or sulfonate group, m is an integer in the range of 3 to 16, p is an integer in the range of 1 to 30, and q is an integer in the range of 1 to 15.

The first region can include a plurality of probe cell regions, and a second region can include a plurality of probe-cell-isolating regions, and the plurality of probe cell regions are surrounded by and separated from each other by the probe-cell-isolating region.

BRIEF DESCRIPTION OF THE DRAWINGS

These and/or other aspects and utilities of the present general inventive concept will become apparent and more readily appreciated from the following description of the embodiments, taken in conjunction with the accompanying drawings of which.

DETAILED DESCRIPTION OF THE PREFERRED EMBODIMENTS

Figure 1:
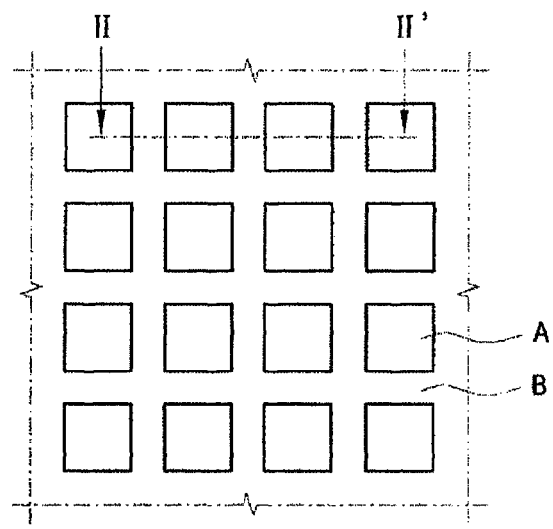
FIG. 1 is a layout view illustrating a microarray according to an embodiment of the present general inventive concept.

Reference will now be made in detail to the embodiments of the present general inventive concept, examples of which are illustrated in the accompanying drawings, wherein like reference numerals refer to the like elements throughout. The embodiments are described below in order to explain the present general inventive concept by referring to the figures.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. Like reference numerals refer to like elements throughout the specification.

The present general inventive concept will be described with reference to perspective views, cross-sectional views, and/or plan views, in which preferred embodiments thereof are illustrated. Thus, the profile of an exemplary view may be modified according to manufacturing techniques and/or allowances. That is, the embodiments described herein are not intended to limit the scope of the present general inventive concept but cover all changes and modifications that can be caused due to a change in manufacturing process.

Microarrays, substrates for the microarrays and methods of fabricating the same according to the present general inventive concept will now be described more fully with reference to the accompanying drawings in which exemplary embodiments of the general inventive concept are shown.

A microarray according to an embodiment of the present general inventive concept will now be described with reference to FIGS. 1 and 2. FIG. 1 is a layout view illustrating a microarray according to an embodiment of the present general inventive concept, and FIG. 2 is a sectional view taken along the line II-II' of FIG. 1.

Figure 2:
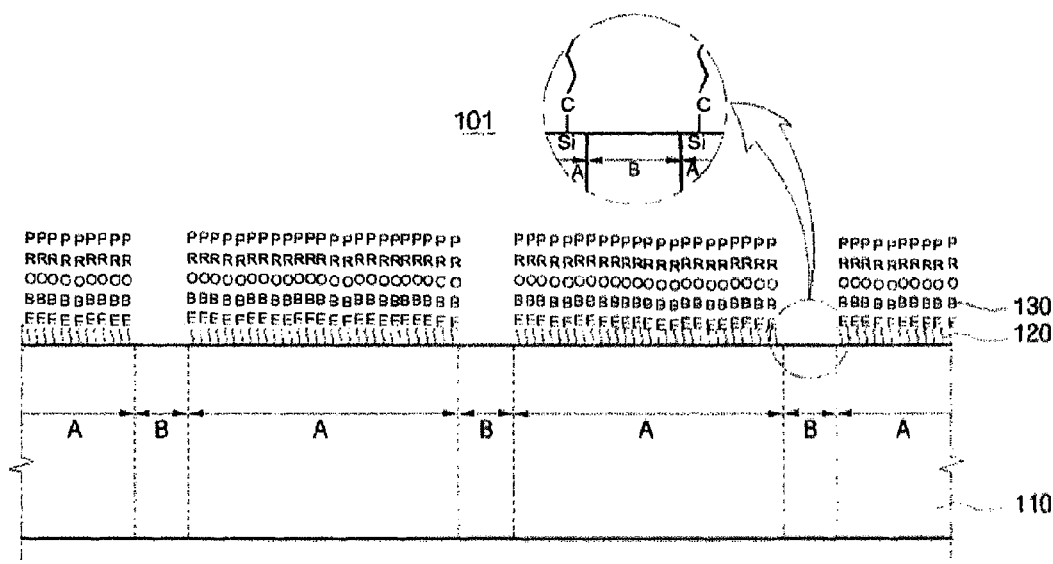
FIG. 2 is a sectional view taken along the line II-II' of FIG. 1.

Referring to FIGS. 1 and 2, the microarray 101 includes a substrate 110, a plurality of linkers 120 directly coupled to the substrate 110 and represented by formula 1 or 2, and a plurality of probes 130 coupled to the respective linkers:

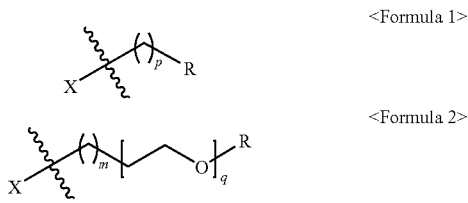

<Formula 1>

<Formula 2> wherein X is a site coupled to the substrate, R is a hydroxyl, aldehyde, carboxyl, amino, amide, thiol, halo, epoxy, or sulfonate group, m is an integer in the range of 3 to 16, p is an integer in the range of 1 to 30, and q is an integer in the range of 1 to 15.

The substrate 110 may be a flexible or rigid substrate. When a flexible substrate is used as the substrate 110, the substrate 110 may be a membrane such as nylon, nitrocellulose and others, or a plastic film and others. When a rigid substrate is used as the substrate 110, the substrate 110 may be a silicone substrate, a transparent glass (e.g., soda-lime glass) substrate, and others. The use of a silicone substrate or a transparent glass substrate as the substrate 110 is advantageous in that non-specific binding hardly occurs during hybridization. Furthermore, a transparent glass substrate is transparent to visible light and/or UV light, and, thus, is advantageous in detection of a fluorescent material. In addition, when a silicone substrate or a transparent glass substrate is used as the substrate 110, it is possible to employ various thin film formation processes and photolithography processes that have been well established and stably applied in the fabrication of semiconductor devices or liquid crystal display (LCD) panels.

The substrate 110 may be divided into a first region and a second region according to whether the linkers 120 are coupled to the substrate 110.

The first region is a region where the linkers 120 are coupled to the substrate 110. Accordingly, at least part of the first region forms a probe cell region A including a plurality of probes. In the second region, the linkers 120 are not coupled to the substrate 110. Consequently, at least part of the second region forms a probe cell isolating region B which separate the probe cell regions A from each other. In an exemplary embodiment illustrated in FIG. 1, the probe cell isolating region B surrounds the probe cell region A, so that the probe cell region A is divided into a plurality of areas. In other words, the probe cell region A may be formed as a distinct cell from other probe cell regions A. The probe cell region may include a plurality of probes (such as the oligomer probes, discussed previously). The probe cell isolating region B is a region that separates or isolates the probe cell regions A from one another.

Since the probe cell region A contains the linkers 120, the probes 130 to which target materials are coupled are arranged in the probe cell region A. Since the probe cell isolating region B does not contain linkers 120, it is difficult for a target sample to nonspecifically bond to the substrate 110. So, the accuracy in detecting the target sample may increase.

The linkers 120 are directly coupled to the substrate 110, as represented by Formula 1 or 2.

In more detail, the linkers 120 have X in Formula 1 or 2, which is a site coupled to the substrate 110. Here, coupling to the substrate 110 can mean chemically binding to, e.g., covalently binding to the substrate 110. In some embodiments of the present general inventive concept, the substrate 110 may be coupled to the linkers 120 by Si—C bonds. The Si—C bonds are sufficiently stable against various chemical or thermal stresses in a subsequent coupling process. Thus, damage to the linkers 120, which may occur in the subsequent process, can be avoided.

In Formula 1 or 2,

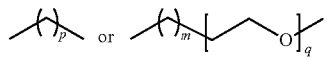

may function as a spacer (not shown). That is,

links the site X coupled with the substrate 110 and the functional group R coupled with the probes 130, and provides a spatial margin for freely interacting, e.g., hybridizing, with target samples. From this standpoint, the linkers 120 may have a sufficient molecular length, e.g., 6-50 atoms. In addition, from the standpoint of noise improvement, at least partly hydrophobic oligo-ethylene glycol groups can be advantageously used. Of course, they are not limited thereto.

The functional groups are groups that can be used as starting points for organic synthesis. That is, the functional groups are groups capable of coupling with the previously synthesized probes 130 or the monomers (e.g., nucleosides, nucleotides, amino acids, or peptides) for in-situ synthesis of the probes 130. The functional groups are not limited to any particular functional groups, provided that they can be coupled to the probes 130 or the monomers for in-situ synthesis of the probes 130. Examples of the functional groups include hydroxyl groups, aldehyde groups, carboxyl groups, amino groups, amide groups, thiol groups, halo groups, and sulfonate groups. In Formula 1 or 2, R is a functional group. That is, the linker 120 is capable of specifically coupling with the probe 130 according to various functional groups contained in the linker 120.

The probe 130 may be, for example, an oligomer probe. As used herein, the term "oligomer" is a low-molecular weight polymer molecule consisting of two or more covalently bound monomers. Oligomers have a molecular weight of about 1,000 or less, but the present invention is not limited thereto. The oligomer may include about 2-500 monomers, and preferably 5-30 monomers. The monomers may be nucleosides, nucleotides, amino acids, peptides, etc. according to the type of probes.

The monomers of the oligomer probe may be, for example, nucleosides, nucleotides, amino acids, or peptides. The nucleosides and nucleotides include not only known purine and pyrimidine bases, but also methylated purines or pyrimidines, acylated purines or pyrimidines, and others. Typical nucleobases are adenine, guanine, cytosine, uracil, and the like. In addition, the nucleosides and nucleotides include not only known (deoxy)ribose, but also a modified sugar which contains a substitution of a halogen atom or an aliphatic group for at least one hydroxyl group or is functionalized with ether, amine, or the like.

The amino acids may be naturally occurring, L-, D-, and nonchiral amino acids, or modified amino acids, amino acid analogs, and others.

The peptides refer to compounds produced by an amide bond between the carboxyl group of one amino acid and the amino group of another amino acid.

Accordingly, the probe 130 may consist of two or more nucleosides, nucleotides, amino acids, or peptides.

In the microarray 101 see FIG. 2 according to an embodiment of the present general inventive concept, the linkers 120 are not coupled to the probe cell isolating region B but coupled to the probe cell region A. Thus, non-specific binding of the target sample can be reduced. In addition, the linkers 120 include sites directly coupled to the substrate 110, and functional groups capable of coupling with spacers and the probes 130. Accordingly, if the linkers 120 are coupled to the substrate 110, providing the microarray 101 capable of coupling to the probes 130 and detecting a target sample without additional structures, the productivity can be further improved.

Figure 3:
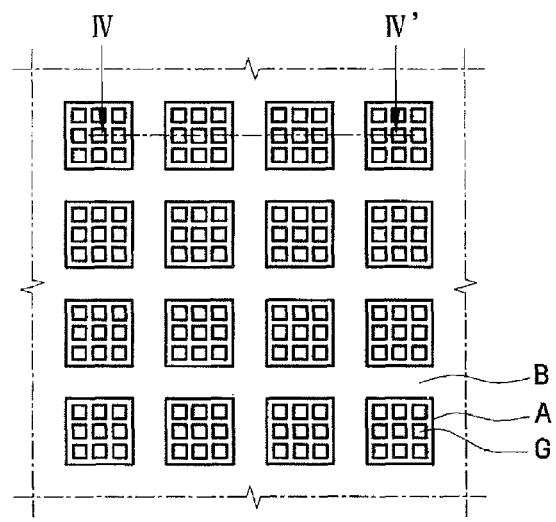
FIG. 3 is a layout view illustrating a microarray according to another embodiment of the present general inventive concept.

Hereinafter, microarrays according to other embodiments will be described with reference to FIGS. 3 through 5. FIG. 3 is a layout view illustrating a microarray according to another embodiment of the present general inventive concept, and FIGS. 4 and 5 are a sectional view taken along the line IV-IV' of FIG. 3, and a sectional view illustrating a microarray according to still another embodiment of the present general inventive concept, respectively.

Figure 4:
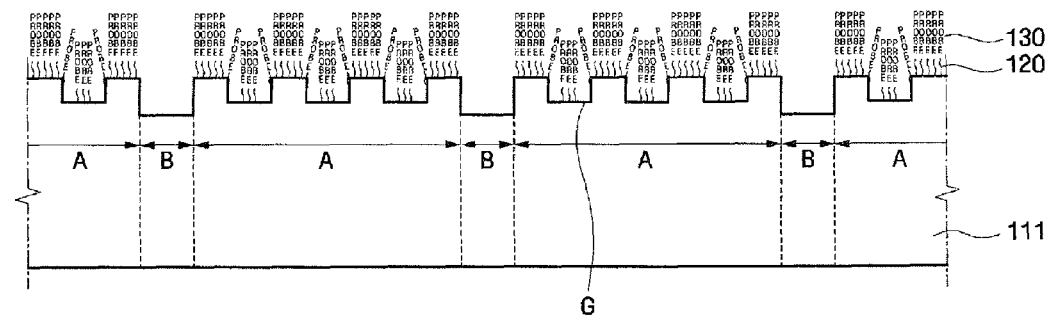
FIG. 4 is a sectional view taken along the line IV-IV' of FIG. 3.
Figure 5:
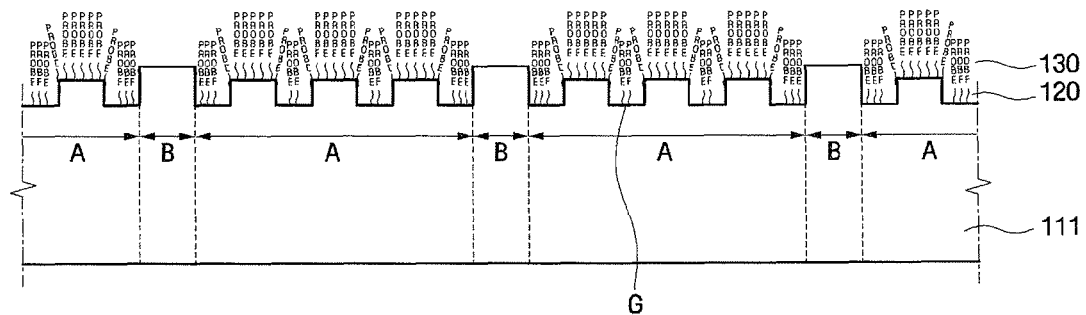
FIG. 5 is a sectional view illustrating a microarray according to still another embodiment of the present general inventive concept.

The microarray 102 (103) see FIGS. 4 and 5 includes a substrate 111 having a three-dimensional surface, a plurality of linkers 120 coupled to the probe cell region A of the substrate 111 and probes 130 coupled to the linkers 120 through functional groups contained in the respective linkers 120.

The microarray according to these embodiments are different from the microarray according to the previous embodiment in that one or more grooves G are arranged in each of the probe cell region A and each probe cell region A has a three-dimensional surface. Here, the three-dimensional surface can mean a three-dimensional structure as a surface formed by one or more grooves G. FIG. 3 illustrates that the grooves G have a square shape. However, it should be understood that the grooves G may have one of various shapes such as a rectangular shape, a circular shape, or a semicircular shape. Although FIG. 3 illustrates that the grooves G having rectangular sections are arranged in serrated forms, it should be understood that the grooves G may be arranged in various forms as long as they provide a three-dimensional structure.

When the surface 111 has a three-dimensional surface, an area capable of coupling with the probes 130 can be increased, and, thus, the number of probes 130 coupled to the respective probe cell areas A can be increased, compared to conventional microarrays having the same design rule as the microarrays of the present invention. Therefore, even when a reduced design rule is employed, desired detection sensitivity can be ensured.

Other characteristics of the components of the microarrays of the other embodiments of the present general inventive concept are substantially the same as those of the previous embodiment, and repeated explanations thereabout will not be given.

Hereinafter, methods of fabricating microarrays according to some embodiments of the general inventive concept will be described.

First, a method of fabricating the microarray illustrated in FIG. 2 will be described with reference to FIGS. 6 through 10.

Figure 6:
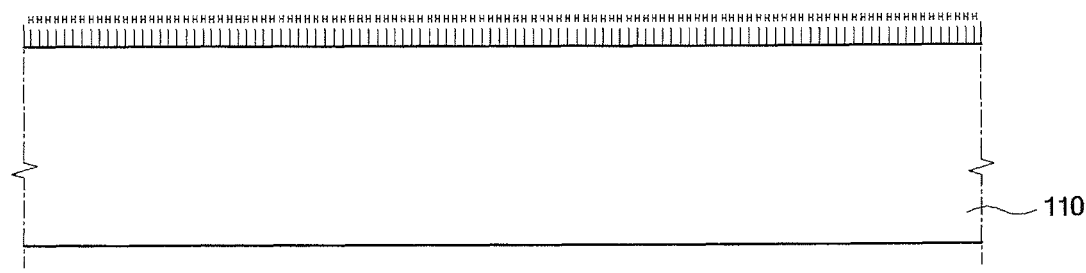
FIGS. 6 through 10 are sectional views of processing steps illustrating a method of fabricating the microarray illustrated in FIG. 2.

Referring to FIG. 6, the substrate 110 having a surface treated with hydrogen fluoride (HF) is provided.

An oxide film may be formed on the surface of the substrate 110, e.g., a silicon (Si) substrate, when the Si substrate is exposed to the air or other causes. In such a case, the substrate 110 is treated with, for example, hydrogen fluoride (HF), to remove the oxide film. Optionally, the HF-treated surface of the substrate 110 may be cleaned. For example, the surface of substrate 110 may be sequentially cleaned using toluene and ethanol, for example. As a result, hydrogen radicals are finally formed on the surface of the substrate 110.

Figure 7:
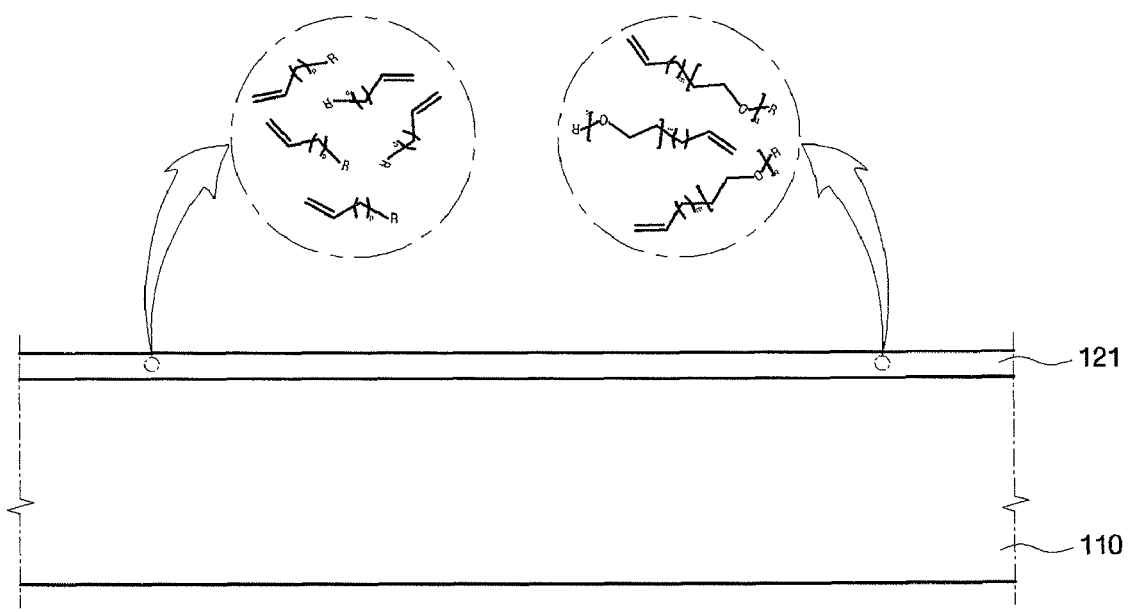

Referring to FIG. 7, a linker compound 121 represented by Formula 3 or 4 is laminated on the substrate 110:

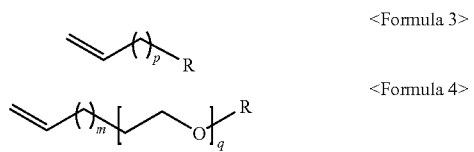

<Formula 3>
<Formula 4> wherein R is a hydroxyl, aldehyde, carboxyl, amino, amide, thiol, halo, epoxy, or sulfonate group, m is an integer in the range of 3 to 16, p is an integer in the range of 1 to 30, and q is an integer in the range of 1 to 15.

The linker compound 121 may be, for example, a 1,2-epoxy-5-hexene solution. The 1,2-epoxy-5-hexene solution can be obtained by dissolving 1,2-epoxy-5-hexene power in a toluene solvent, and processing it with nitrogen gas for about 30 minutes. However, the method of obtaining the linker compound 121 is not limited to the illustrated example. For example, the lamination method of the linker compound 121 may be a spin-coat method, but is not limited thereto.

Figure 8:
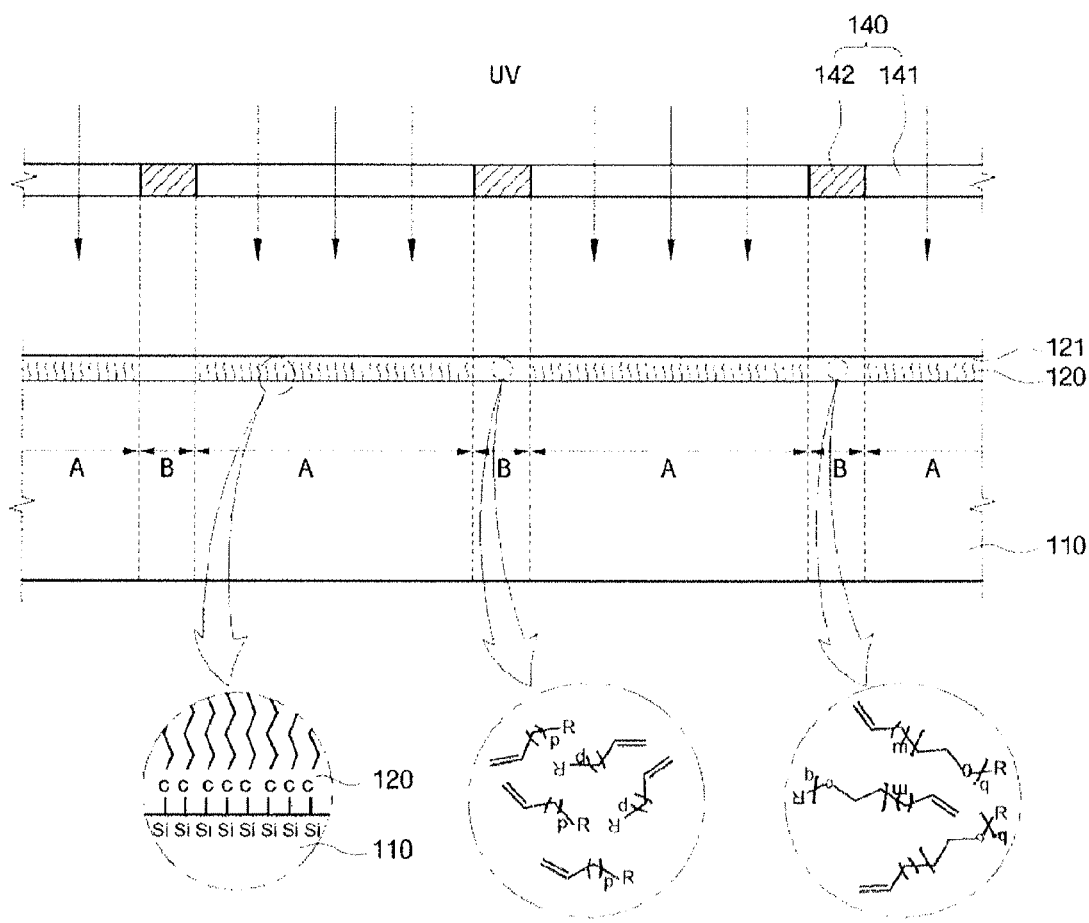

Referring to FIG. 8, UV light may be optionally radiated onto the linker compound 121.

The linker compound 121 represented by Formula 3 or 4 includes a carbon-carbon double bond. When external energy, e.g., heat or UV light, is applied, the carbon-carbon double bond of the linker compound 121 interacts with the hydrogen radicals formed on the surface of the substrate 110 so that there may be formed a Si—C bond. The external energy may be, e.g., light (UV light) having a wavelength of about 365 nm and an energy of about 25 mW/cm². Here, the linker compound 121 may be exposed to UV light for about 10 minutes.

When the linker compound 121 is exposed to UV light, the UV light is selectively radiated using a mask 140 having a transmission region 141 and a shielding region 142. Here, since only the linker compound 121 exposed to UV light is converted to the linkers 120 coupled to the substrate 110, the mask 140 is arranged such that the transmission region 141 of the mask 140 is aligned with the probe cell region A. If the UV light is radiated in a state in which the mask 140 is arranged, the linkers 120 are formed in an area aligned with the transmission region 141, while the linker compound 121 still exists in an area aligned with the shielding region 142.

Figure 9:
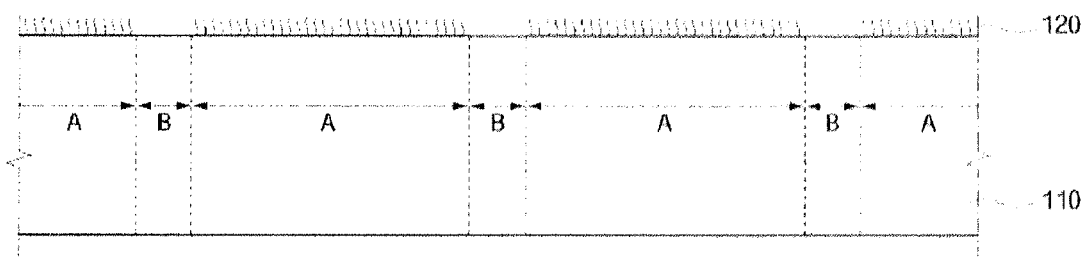

Referring to FIG. 9, the unexposed linker compound (121 of FIG. 8) is removed by a cleaning process. The cleaning process may be performed by cleaning the substrate 110 sequentially by toluene, ethanol, and water. After the cleaning process, the resultant substrate 110 includes probe cell regions A including the linkers 120 and probe cell isolating regions B without the linkers 120.

Here, since the linkers 120 are not coupled to the probe cell isolating region B, the surface of the substrate 110 is exposed. As described above, the surface of the substrate 110 is treated with HF and the hydrogen radical is formed thereon. However, while the substrate 110 undergoes various processes, the hydrogen radical, which is highly reactive, reacts with air, so that the hydrogen radical on the surface of the substrate 110 may be converted into a hydroxyl group, which is present on a general surface of a substrate. As a result, coupling occurs between a target sample and the probe cell region A of the substrate 110 much more vigorously than between the target sample and the probe-cell-isolating region B, thereby increasing the accuracy in detecting the target sample.

After completing the cleaning process, a substrate 201 for a microarray illustrated in FIG. 9 is obtained as an intermediate structure. The microarray substrate 201 according to an embodiment of the present general inventive concept has a probe cell region A defined by a probe-cell-isolating region B, thereby reducing non-specific binding between the target sample and the substrate 110, thereby increasing the accuracy in detecting the target sample.

In addition, the linkers 120 include both coupling sites capable of directly coupling to the substrate 110 and functional groups capable of coupling to probes. Accordingly, since the microarray 201 capable of coupling to the probes and detecting a target sample is provided without additional structures, the productivity can be further improved.

Figure 10:
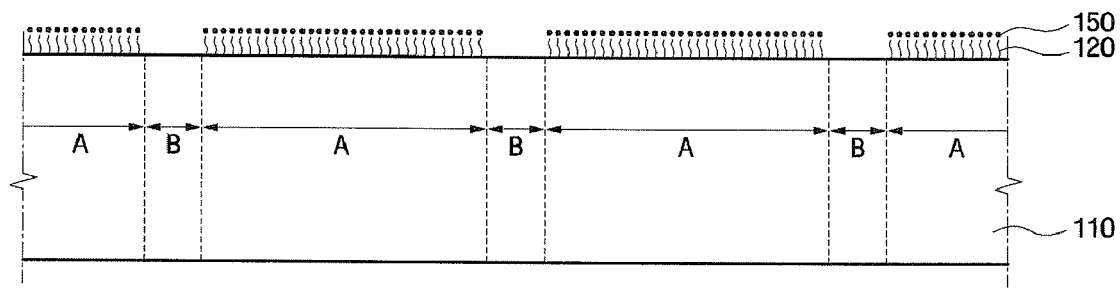

Referring to FIG. 10, protecting groups 150 are coupled to functional groups (not shown) of the linkers 120. In detail, the protecting groups 150 are formed on the entire surface of the substrate 110 to couple with the functional groups of the linkers 120. The term "protecting group" can mean a group that blocks a coupling site from participating in a chemical reaction, and the term "deprotection" can mean removal of the protecting group so as to allow the coupling site to participate in a chemical reaction. That is, the protecting groups 150 may be coupled to functional groups of the linkers 120 to protect the functional groups. Then, the protecting groups 150 may be removed before monomers used for in-situ photolithographic synthesis or the probes coupled to expose the functional groups. Since the protecting groups 150 are acid-labile or photolabile protecting groups, they can be deprotected by acid or photo.

Referring to FIG. 2, the probes 130 are coupled to the linkers 120. The probes 130 may be synthesized in advance, or by coupling using in-situ synthesis of monomers for probes. More detailed procedures for the in-situ synthesis and coupling of the probes 130 can be easily deduced from the method well known in the art, and a detailed explanation will not be given. After the coupling between the probes 130 and the linkers 120 is completed, the microarray 101 illustrated in FIG. 2, is fabricated.

According to the fabrication method of the microarray according to an embodiment of the present general inventive concept, hydroxyl groups are contained on the surface of the probe cell isolating region B, which reduces non-specific binding of a target sample, thereby providing a microarray having improved accuracy in detecting the target sample. In addition, the present invention provides a microarray including linkers having sites directly coupled to the substrate, spacers and functional groups, thereby allowing the microarray to detect a target sample without additional structures.

Hereinafter, a method of fabricating the microarray illustrated in FIG. 4 will be described with reference to FIG. 11 through 15.

FIG. 11 through 15 are sectional views of processing steps illustrating a method of fabricating the microarray illustrated in FIG. 4, in particular, a method of fabricating a substrate including a three-dimensional surface.

The method of fabricating the microarray according to the current embodiment is different from that according to the previous embodiment in that the substrate 111 has a three-dimensional surface. That is, in the microarry fabrication method illustrated in FIGS. 11 through 15 in which the substrate 111 has a three-dimensional surface, an area capable of coupling with probes can be increased, compared to a microarray having the same design rule, thereby ensuring desired detection sensitivity even when a reduced design rule is employed.

Figure 11:
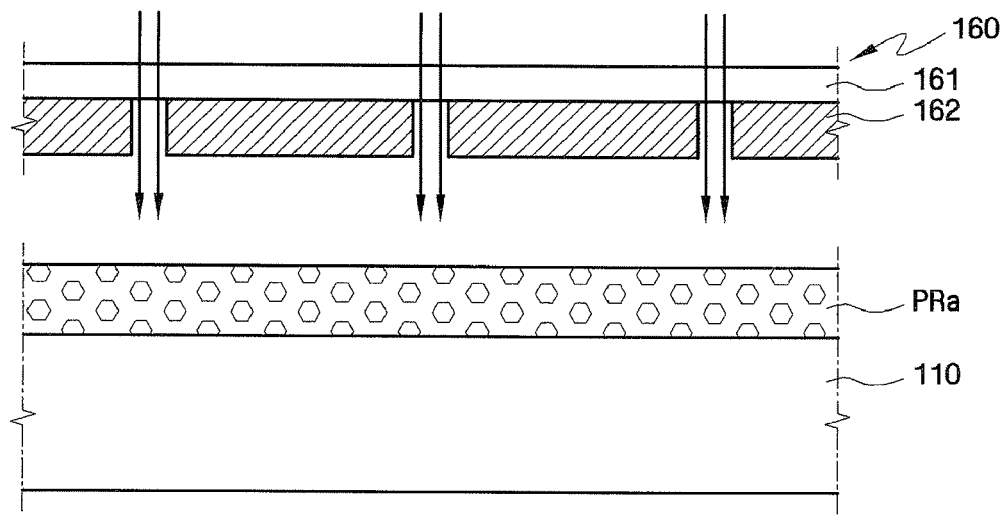
FIGS. 11 through 15 are sectional views of processing steps illustrating a method of fabricating the microarray illustrated in FIG. 4.

As illustrated in FIG. 11, a photoresist layer PRa may be formed on the substrate 110.

Although not illustrated, in order to facilitate formation of a three-dimensional pattern, a polymer layer may be formed on the substrate 110. The polymer layer may be made of, for example, a silicon oxide film such as a PE-TEOS film, a HDP oxide film, a P—SiH$_4$ oxide film or a thermal oxide film; silicate such as hafnium silicate or zirconium silicate; a metallic oxynitride film such as a silicon nitride film, a silicon oxynitride film, a hafnium oxynitride film or a zirconium oxynitride film; a metal oxide film such as ITO; a metal such as gold, silver, copper or palladium; polyimide; polyamine; or polymers such as polystyrene, polyacrylate or polyvinyl.

Here, a photoresist film PRa is exposed to light using a projection exposure machine. The projection exposure machine employs a mask pattern 160 designed to form a desired three-dimensional pattern on a surface of the substrate 110. While FIG. 11 illustrates the mask pattern 160 is a checkerboard type mask constructed such that a light-shielding patterns 162 is formed on a transparent substrate 161 to define probe cell active regions, the shapes of the light-shielding patterns 162 may vary according to the type of the photoresist film PRa.

Figure 12:
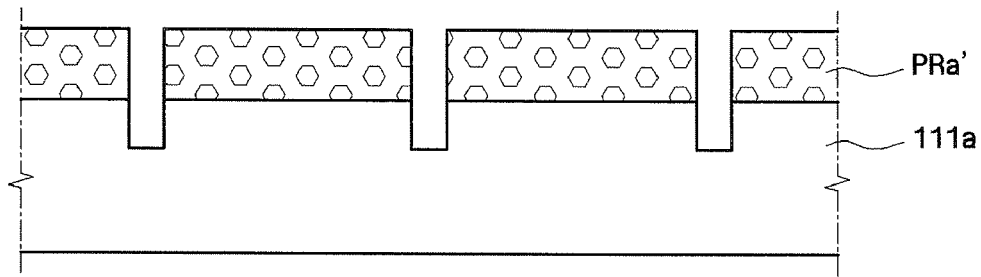

As illustrated in FIG. 12, the exposed photoresist film PRa is developed to form a photoresist pattern PRa'. Then, a surface of a substrate 111a is primarily etched using the photoresist pattern PRa' as an etching mask, thereby primarily modifying the surface of the substrate 111a.

Figure 13:
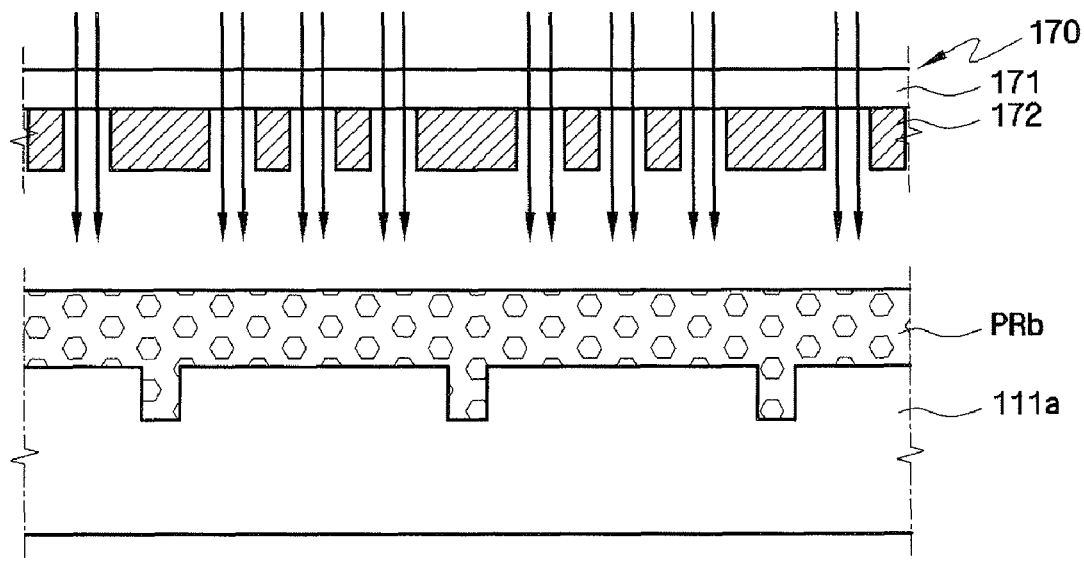

Referring to FIG. 13, in order to form a more elaborate three-dimensional surface, a photoresist film PRb may be formed on the primarily modified surface of the substrate 111a. Like in the previous embodiment, the photoresist film PRb is exposed to light using a projection exposure machine. While FIG. 13 illustrates a mask pattern 170 used is a mask having a checkerboard type exposure area, the shapes of light-shielding patterns 172 of the mask may vary according to the type of the photoresist film PRb.

Figure 14:
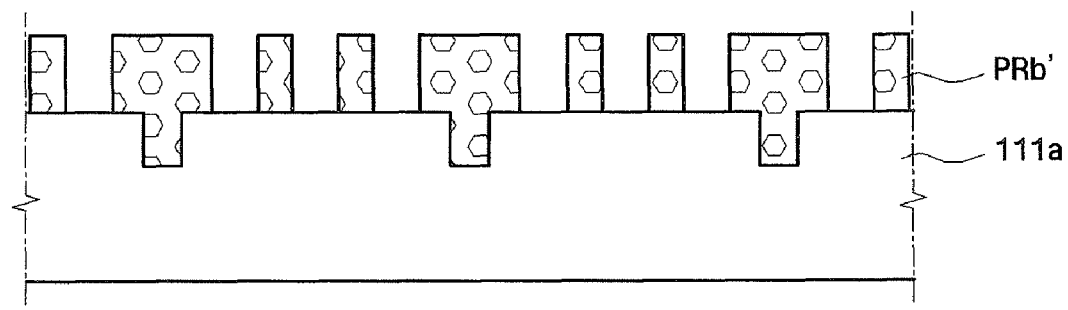
Figure 15:
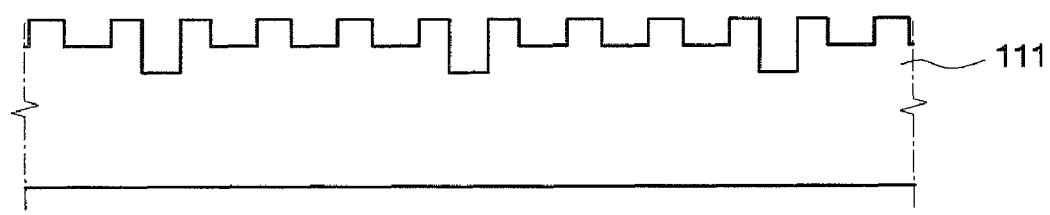

Referring to FIGS. 14 and 15, the exposed photoresist film PRb is developed to form a photoresist pattern PRb', and a surface of a modified substrate 111a is further etched using the photoresist pattern PRb' as an etching mask to secondarily modify the surface of the substrate 111a, thereby fabricating the substrate 111 having a three-dimensional surface.

While FIGS. 11 through 15 illustrate the substrate having a three-dimensional surface formed using a mask twice (that is, the mask patterns 160 and 170), the number of times the mask is used and the shapes of the mask patterns may vary.

According to the method of fabricating the microarray according to the current embodiment, in which the substrate has a three-dimensional surface, an area capable of coupling with probes can be increased, compared to conventional microarrays having the same design rule. Accordingly, the number of probes coupled can be increased, thereby allowing the microarray to ensure desired detection sensitivity even when a reduced design rule is employed.

Figure 16:
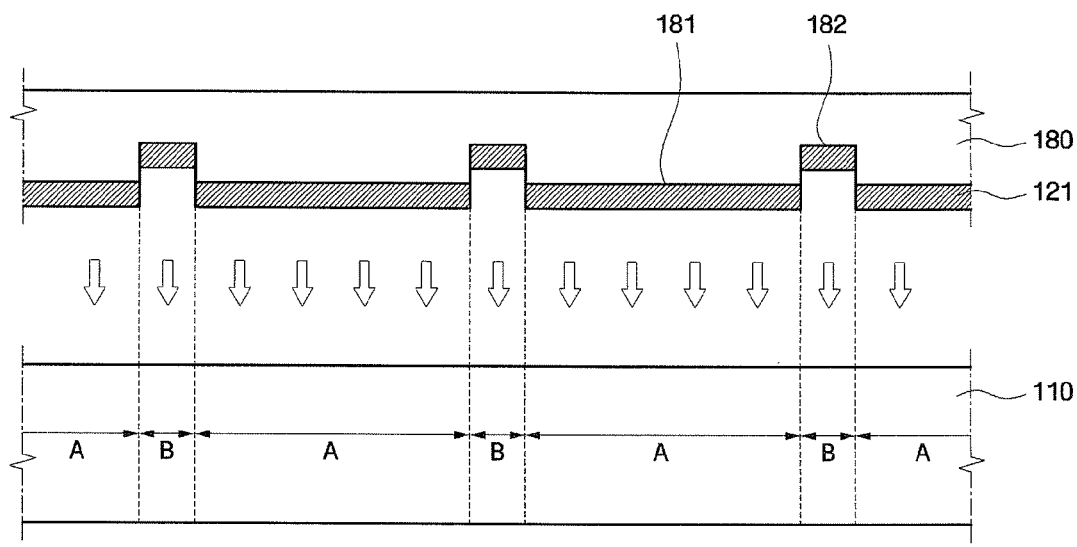
FIGS. 16 and 17 are sectional views of processing steps illustrating a method of fabricating the microarray according to another embodiment of the present general inventive concept.
Figure 17:
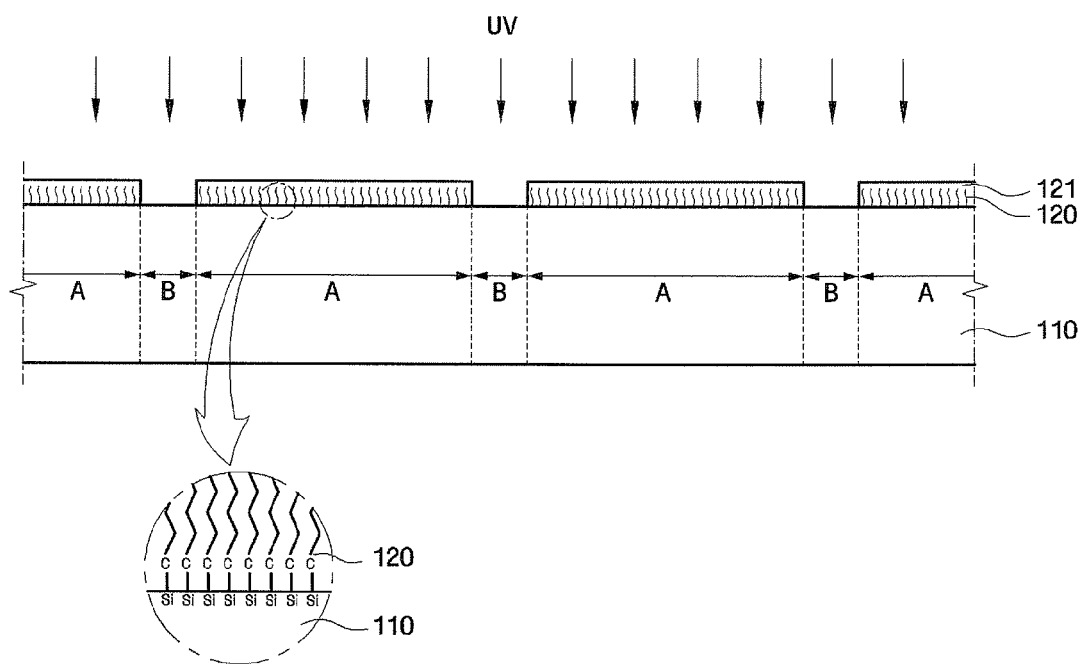

Hereinafter, a method of fabricating a microarray according to still another embodiment of the present general inventive concept will be described with reference to FIGS. 16 and 17. FIGS. 16 and 17 are sectional views of processing steps illustrating the method of fabricating the microarray. The method of fabricating the microarray according to the current embodiment illustrated in FIGS. 16 and 17 is substantially the same as the previous embodiment illustrated in FIGS. 2 through 6, except for a method of laminating the linker compound 121 on the substrate 110, and therefore a detailed explanation thereof will not be given.

Referring to FIG. 16, a stamp 180 having a linker compound 121 formed on its surface is brought into contact with a substrate 110.

Although not illustrated, the stamp 180 may be fabricated using a separate master pattern. For example, a master pattern having a predetermined roughness is formed on a silicon substrate by E-beam radiation or photolitograpy, and a prepolymer is coated to the master pattern. Next, the prepolymer is hardened in a chemical manner, e.g., using a curing agent, the hardened prepolymer is then peeled off from the mater pattern, thereby fabricating the stamp 180. Here, the predetermined roughness of the stamp 180 may be formed to correspond to the probe cell isolating region B and probe cell region A; the probe cell region A corresponding to a convex portion 181 of the stamp 180, and the probe cell isolating region B corresponding to a concave portion 182 of the stamp 180, respectively.

Next, the linker compound 121 is formed on a surface of the stamp 180 and the stamp 180 is brought into contact with the substrate 110 so that the linker compound 121 is transferred to the substrate 110. Here, since only a convex portion 181 of the stamp 180 is in contact with the substrate 110, the linker compound 121 provided on the convex portion 181 is transferred to the substrate 110. That is, even if the linker compound 121 is provided on the concave portion 182 of the stamp 180, the linker compound 121 on the surface of the concave portion 182 is not transferred to the substrate 110 because the concave portion 182 is not in contact with the substrate 110. As described above, without using a mask, by using the stamp 180 having the convex portion 181 and the concave portion 182 corresponding to the probe cell region A and the probe cell isolating region B, the linker compound 121 can be transferred selectively only to the probe cell region A of the substrate 110.

Referring to FIG. 17, UV light is radiated onto the linker compound 121 having a predetermined pattern on the substrate 110, thereby forming linkers 120 directly coupled to the substrate 110. As described above, since the linker compound 121 is not provided in the probe cell isolating region B, it is not necessary to use a mask (140 of FIG. 8) when the UV light is radiated. Since the process is simplified, the processing efficiency and the processing speed are improved and microarrays can be produced in a much more cost-effective manner. Next, a process of coupling probes to the linkers 120 is substantially the same as that described above with reference to the previous embodiments.

Furthermore, although not illustrated, a master pattern is formed on a transparent substrate by E-beam radiation or photolithograpy, and a prepolymer is laminated on the master pattern. The master pattern is brought into contact with a substrate 110 having the prepolymer laminated thereon, wherein the prepolymer may fill a mask pattern. Thereafter, the prepolymer is cured by UV radiation. Then, in order to remove the hardened prepolymer from the mater pattern using, e.g., a nano imprinting method, linkers 120 may be formed in a probe cell region A.

Since the microarray fabrication method according to still another embodiment of the present general inventive concept provides a microarray having finer patterns of the probe cell region and the probe cell isolating region, the fabricated microarray can have an increased integration level.

Figure 18:
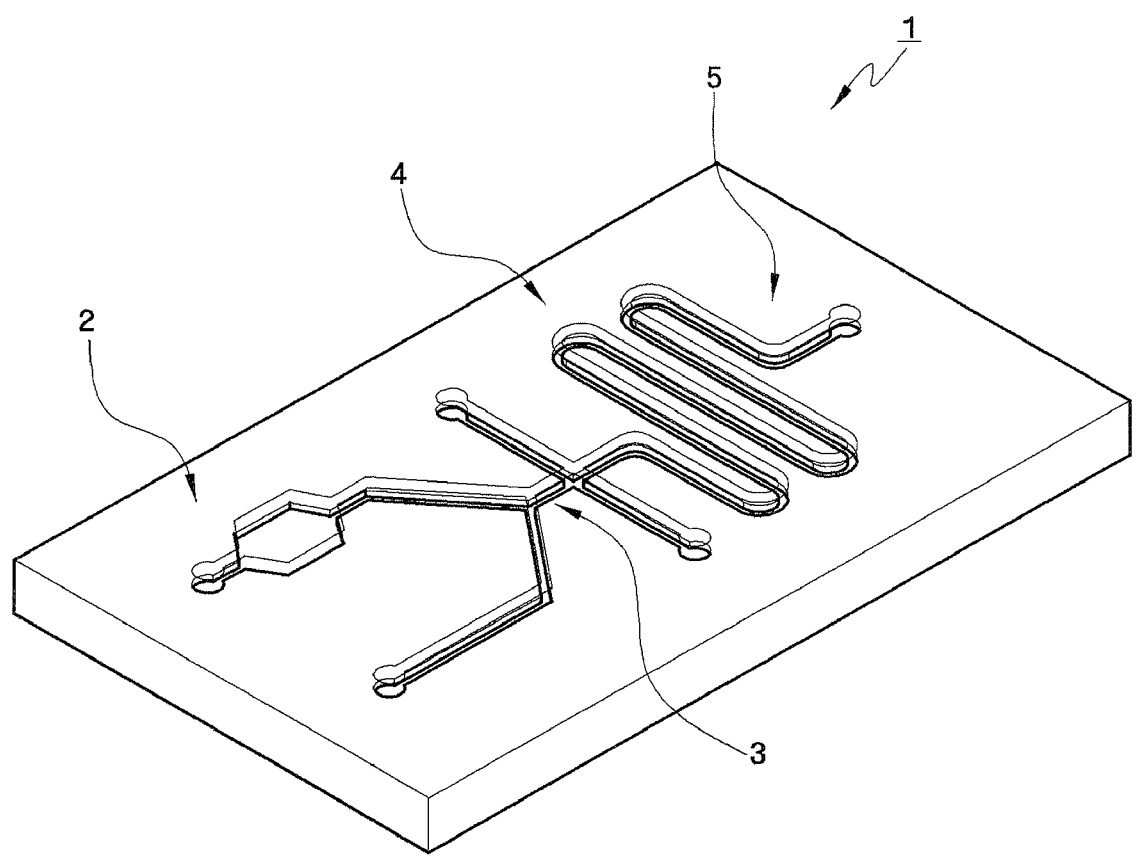
FIG. 18 is a conceptual diagram of a lap-on-a-chip.

The concept of Lab-On-a-Chip (LOC) can be applied to the microarrays according to some embodiments of the present general inventive concept and fabrication methods thereof, and it is possible to integrate a plurality of different laboratory operations in a single chip by directly using a variety of samples of biomolecules, chemicals or natural molecules. As such, the microarrays according to some embodiments of the present general inventive concept and fabrication methods thereof can be utilized in a wide variety of applications, including research, diagnosis and treatment purposes. As illustrated in FIG. 18, a Lab-on-a-chip (LOC) 1 includes a preprocessor 2, a reaction unit 3, an extraction/analysis unit 4 and a detector 5.

If a small amount of an experimental fluid is introduced into a microfluidic channel of a chip through an orifice, the preprocessor 2 carries out an appropriate treatment on the experimental fluid. Thereafter, the experimental fluid is transferred to the reaction unit 3 using power driven by an electrical signal or a microcompressor to cause a reaction with a chemical material producing a fluorescent material in the reaction unit 3. Next, the result of the reaction is subjected to computer-based analysis in the extraction/analysis unit 4 and the detector 5.

During this procedure, a microarray can be used. If the microarray is used in combination with LOC, an effective and immediate reaction can be caused by introduction of a tiny amount of sample (e.g., in a 1/1000 one nanoliter scale), thereby improving the sensitivity and accuracy in target sample detection.

As described above, since the microarrays according to embodiments of the present general inventive concept include both coupling sites capable of directly coupling to a substrate and functional groups capable of coupling to probes, the microarrays are capable of coupling to the probes without additional structures, thereby further improving the productivity of the manufacturing process. The interaction between the microarrays according to embodiments of the present general inventive concept and target samples can be improved according to the length of linkers and functional groups used, thereby further enhancing the reactivity.

According to the microarray fabrication method of the present general inventive concept, while linkers coupled to a substrate are formed, a probe cell region and a probe-cell-isolating region are formed on the substrate, thereby reducing the processing time and ultimately improving the processing efficiency. Accordingly, the productivity can be further improved. In addition, since linkers are not coupled to the probe-cell-isolating region, no functional groups are present in the linkers, and non-specific binding between the target sample and the substrate decrease, thereby providing microarrays having improved accuracy in detecting the target sample.

Although a few embodiments of the present general inventive concept have been shown and described, it will be appreciated by those skilled in the art that changes may be made in these embodiments without departing from the principles and spirit of the general inventive concept, the scope of which is defined in the appended claims and their equivalents.

What is claimed is:

1. A microarray comprising;
   a substrate divided into a first region and a second region;
   a plurality of linkers represented by formula 1 or 2, directly coupled to the substrate in the first region but not coupled to the substrate in the second region, the linkers forming a substantially contiguous layer on a surface of the first region of the substrate; and
   a plurality of probes coupled to the respective linkers:

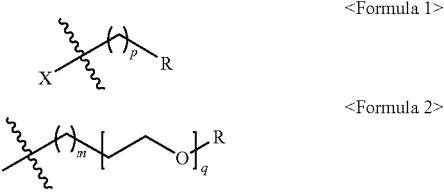

wherein X is a site coupled to the substrate, R is a hydroxyl, aldehyde, carboxyl, amino, amide, thiol, halo, epoxy, or sulfonate group, m is an integer in the range of 3 to 16, p is an integer in the range of 1 to 30, and q is an integer in the range of 1 to 15.

2. The microarray of claim 1, wherein the linkers are coupled to the substrate by Si—C bonds.

3. The microarray of claim 1, wherein the first region includes a three-dimensional surface.

4. The microarray of claim 1, wherein the first region includes a plurality of probe cell regions, and the second region includes a probe-cell-isolating region, the plurality of probe cell regions are surrounded by and separated from each other by the probe-cell-isolating-region.

5. A substrate for a microarray, comprising;
a substrate divided into a first region and a second region; and
a plurality of linkers represented by formula 1 or 2, directly coupled to the substrate in the first region but not coupled to the substrate in the second region, the linkers forming a substantially contiguous layer on a surface of the first region of the substrate:

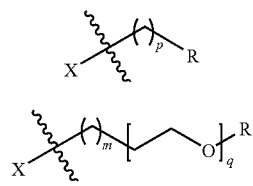

<Formula 1>
<Formula 2> wherein X is a site coupled to the substrate, R is a hydroxyl, aldehyde, carboxyl, amino, amide, thiol, halo, epoxy, or sulfonate group, m is an integer in the range of 3 to 16, p is an integer in the range of 1 to 30, and q is an integer in the range of 1 to 15.

6. A method of fabricating a microarray, comprising:
providing a substrate divided into a first region and a second region, the substrate having a hydrogen radical on its surface;
directly coupling a plurality of linkers represented by formula 1 or 2 to the substrate in the first region; and
coupling a plurality of probes to the respective linkers:

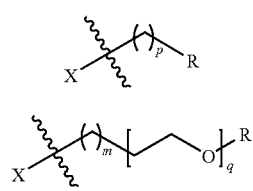

<Formula 1>
<Formula 2> wherein X is a site coupled to the substrate, R is a hydroxyl, aldehyde, carboxyl, amino, amide, thiol, halo, epoxy, or sulfonate group, m is an integer in the range of 3 to 16, p is an integer in the range of 1 to 30, and q is an integer in the range of 1 to 15.

7. The method of claim 6, wherein the linkers are coupled to the substrate by Si—C bonds.

8. The method of claim 6, wherein the first region includes a three-dimensional surface.

9. The method of claim 6, wherein the first region includes a plurality of probe cell regions, and the second region includes a probe-cell-isolating region, the plurality of probe cell regions are surrounded by and separated from each other by the probe-cell-isolating region.

10. A method of fabricating a microarray, comprising:
providing a substrate divided into a first region and a second region;
laminating the substrate with a linker compound represented by formula 3 or 4:

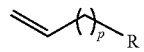
<Formula 3>

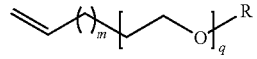
<Formula 4> wherein R is a hydroxyl, aldehyde, carboxyl, amino, amide, thiol, halo, epoxy, or sulfonate group, m is an integer in the range of 3 to 16, p is an integer in the range of 1 to 30, and q is an integer in the range of 1 to 15;
forming a plurality of linkers directly coupled to the substrate by selectively radiating UV light onto the linker compound; and
coupling probes to the plurality of linkers, respectively.

11. The method of claim 10, wherein the providing of the substrate comprises providing the substrate having a surface treated with hydrogen fluoride (HF).

12. The method of claim 10, wherein the selectively radiating of the UV light comprises aligning a mask having a transmission region and a shielding region, such that the transmission region of the mask is aligned with the first region and the shielding region is aligned with the second region.

13. The method of claim 10, wherein the linker is represented by formula 1 or 2:

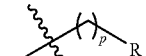
<Formula 1>

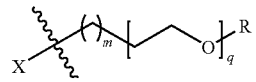
<Formula 2> wherein X is a site coupled to the substrate, R is a hydroxyl, aldehyde, carboxyl, amino, amide, thiol, halo, epoxy, or sulfonate group, m is an integer in the range of 3 to 16, p is an integer in the range of 1 to 30, and q is an integer in the range of 1 to 15.

14. The method of claim 10, further comprising:
removing the linker compound remaining on the surface by performing a cleaning process, after selectively radiating the UV light.

15. The method of claim 10, further comprising:
coupling a protecting group to a terminal of each of the plurality of linkers after the forming of the plurality of linkers.

16. The method of claim 10, wherein the laminating of the linker compound comprises:
forming the linker compound on a surface of a stamp; and
contacting the stamp with the substrate so that the linker compound is transferred to the substrate.

17. The method of claim 16, wherein the stamp includes a concave portion and a convex portion, and wherein the contacting of the stamp with the substrate is performed such that the convex portion of the stamp contacts the first region of the substrate and the convex portion of the stamp does not contact the substrate.

18. The method of claim 10, wherein the first region includes a three-dimensional surface.

19. A method of fabricating a microarray, comprising:
directly coupling a plurality of linkers represented by formula 1 or 2 to a first region of a substrate having a hydrogen radical on its surface; and coupling a plurality of probes to the respective linkers:

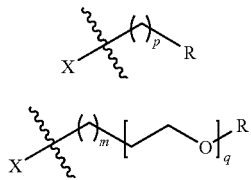

<Formula 1>

<Formula 2> wherein X is a site coupled to the substrate, R is a hydroxyl, aldehyde, carboxyl, amino, amide, thiol, halo, epoxy, or sulfonate group, m is an integer in the range of 3 to 16, p is an integer in the range of 1 to 30, and q is an integer in the range of 1 to 15.

20. The method of claim 19, wherein the first region includes a plurality of probe cell regions, and a second region includes a plurality of probe-cell-isolating regions, and the plurality of probe cell regions are surrounded by and separated from each other by the probe-cell-isolating region.

21. The method of claim 6, wherein the linkers form a substantially contiguous layer on a surface of the first region of the substrate.

22. The method of claim 10, wherein the linkers form a substantially contiguous layer on a surface of the first region of the substrate.

23. The method of claim 19, wherein the linkers form a substantially contiguous layer on a surface of the first region of the substrate.

* * * * *